US012579423B2

(12) United States Patent
Naik et al.

(10) Patent No.:  US 12,579,423 B2
(45) Date of Patent:      Mar. 17, 2026

(54) SYSTEMS AND METHODS FOR PREDICTING BIOLOGICAL RESPONSES

(71) Applicant: Sanofi Pasteur, Inc., Swiftwater, PA (US)

(72) Inventors: Armaghan Waseem Naik, Cambridge, MA (US); Mario Barro, Reading, MA (US); Dustin Holloway, Natick, MA (US); Konstantin Zeldovich, Belmont, MA (US); Tod Strugnell, Carlisle, MA (US); Philip Davidson, Watertown, MA (US); William Warren, Orlando, FL (US)

(73) Assignee: Sanofi Pasteur, Inc., Swiftwater, PA (US)

( * ) Notice: Subject to any disclaimer, the term of this patent is extended or adjusted under 35 U.S.C. 154(b) by 1018 days.

(21) Appl. No.: 17/075,501

(22) Filed: Oct. 20, 2020

(65) Prior Publication Data

US 2021/0117789 A1      Apr. 22, 2021

Related U.S. Application Data

(60) Provisional application No. 62/924,079, filed on Oct. 21, 2019.

(51) Int. Cl.
G06N 3/08          (2023.01)
G06N 3/04          (2023.01)
(Continued)

(52) U.S. Cl.
CPC ................. G06N 3/08 (2013.01); G06N 3/04 (2013.01); G16B 5/20 (2019.02); G16B 30/10 (2019.02); G16B 40/00 (2019.02)

(58) Field of Classification Search
CPC ... G06N 3/08; G06N 3/04; G16B 5/20; G16B 30/10; G16B 40/00; G16H 50/80; G16H 50/20
See application file for complete search history.

(56) References Cited

U.S. PATENT DOCUMENTS

2005/0262031 A1*  11/2005  Saidi ....................... G16Z 99/00
                                                        600/407
2005/0282148 A1    12/2005  Warren et al.
                        (Continued)

FOREIGN PATENT DOCUMENTS

CA          2826894        8/2012
CN          103493057      1/2014
                (Continued)

OTHER PUBLICATIONS

Xu et al. "Artificial neural networks for immunological recognition" Aug. 10, 2018, arXiv.org, https://doi.org/10.48550/arXiv.1808.03386 (Year: 2018).*
(Continued)

*Primary Examiner* — James D. Rutten
(74) *Attorney, Agent, or Firm* — Fish & Richardson P.C.

(57)                    ABSTRACT

Systems and methods can apply machine learning techniques to predict biological responses. One of the methods is performed by at least one processor executing executable logic including at least one machine learning model trained to predict biological responses. The method includes receiving first sequence data of a first molecular sequence, receiving second sequence data of a second molecular sequence, and predicting a biological response for the second molecular sequence based at least partly on the received first and second sequence data.

20 Claims, 5 Drawing Sheets

(51) Int. Cl.

| | |
|---|---|
| *G16B 5/20* | (2019.01) |
| *G16B 30/10* | (2019.01) |
| *G16B 40/00* | (2019.01) |

(56) References Cited

U.S. PATENT DOCUMENTS

| | | | |
|---|---|---|---|
| 2006/0259249 A1* | 11/2006 | Sampath | G16B 40/00 |
| | | | 702/20 |
| 2006/0270029 A1 | 11/2006 | Warren et al. | |
| 2006/0275270 A1 | 12/2006 | Warren et al. | |
| 2007/0141552 A1 | 6/2007 | Warren et al. | |
| 2009/0299767 A1* | 12/2009 | Michon | G16H 50/70 |
| | | | 707/999.005 |
| 2010/0178676 A1 | 7/2010 | Warren et al. | |
| 2014/0052428 A1 | 2/2014 | Naik et al. | |
| 2018/0107927 A1* | 4/2018 | Frey | G06N 3/08 |
| 2021/0391031 A1* | 12/2021 | Malone | G16B 40/20 |

FOREIGN PATENT DOCUMENTS

| | | |
|---|---|---|
| WO | WO 2011/119484 | 9/2011 |
| WO | WO 2012112534 | 8/2012 |

OTHER PUBLICATIONS

Bowman et al. "Improving reverse vaccinology with a machine learning approach" Vaccine, vol. 29, Issue 45, 2011, pp. 8156-8164, ISSN 0264-410X, https://doi.org/10.1016/j.vaccine.2011.07.142. (Year: 2011).*

Calis JJA, Maybeno M, Greenbaum JA, Weiskopf D, De Silva AD, et al. (2013) Properties of MHC Class I Presented Peptides That Enhance Immunogenicity. PLOS Computational Biology 9(10): e1003266. https://doi.org/10.1371/journal.pcbi.1003266 (Year: 2013).*

Lee et al., "Identifying potential immunodominant positions and predicting antigenic variants of influenza A/H3N2 viruses", Vaccine, Nov. 2007, 25(48): 8133-8139.

PCT International Search Report and Written Opinion in International Application No. PCT/US2020/056525, dated Feb. 10, 2021, 17 pages.

Zhou et al., "A generalized approach to predicting protein-protein interactions between virus and host", BMC Genomics, Aug. 2018, 19(suppl 6): 568, 9 pages.

International Preliminary Report on Patentability in International Application No. PCT/US2020/056525, dated May 5, 2022, 10 pages.

Nandy et al., "Bioinformatics in Design of Antiviral Vaccines," Encyclopedia of Biomedical Engineering, Sep. 2019, 3:280-290.

Si et al., "Construction and characterization of a Helicoverpa armigera nucleopolyhedrovirus bacterial artificial chromosome with deletion of ecdysteroid UDP-glucosyltransferase," Chinese Academy of Sciences, Oct. 31, 2016, p. 103 (English abstract only).

Li et al., "Computer-Assisted Molecular Biology Experiment Design and Analysis" Military Medical Science Press, Apr. 1, 2009, 1 page (English Abstract only).

* cited by examiner

CYCLE 1

| Model | Antigens | Assays | Read-Out Panel | Total Readouts (Titers) |
|---|---|---|---|---|
| Ferret | 90 H3N1 Virus | HAI/AF | 18 Strains (1950s-Present) | 3200 HAI / 3200 AF |
| Mouse | 90 H3 rHA+AF03 | HAI/AF | 18 Strains (1950s-Present) | 1600 HAI/ 1600 AF |
| MIMIC | 90 H3 rHA | HAI/AF | 18 Strains (1950s-Present) | 13000 SA-HAI/ 13000 AF |

CYCLE 2

| Model | Antigens | Assays | Read-Out Panel | Total Readouts (Titers) |
|---|---|---|---|---|
| Ferret | 9 H3N1 Virus | HAI/AF | 57 Strains (2009-Present) | 800 HAI / 1000 AF |
| Mouse | 9 H3 rHA+AF03 | HAI/AF | 57 Strains (2009-Present) | 400 HAI/ 500 AF |
| MIMIC | 9 H3 rHA | HAI/AF | 57 Strains (2009-Present) | 3200SA-HAI/ 4100 AF |

FIG. 3

Input: Sequences of Inoculation Strain (First Protein) and Readout Strain (Second Protein) encoded as amino acid mismatches
{00100010010110111}
{00111011010111000}
{00000000100010000}
401

Input: Ferret AF Titers (Cycles 1 and 2) 402

Input: Mouse AF Titers (Cycles 1 and 2) 403

Input: Human Titers (Target Prediction) 404

Row 1: Inoculation/ Readout Pair 1

Row 2: Inoculation/ Readout Pair 2

Row 3: Inoculation/ Readout Pair 3

400

SYSTEMS AND METHODS FOR PREDICTING BIOLOGICAL RESPONSES

CROSS-REFERENCE TO RELATED APPLICATIONS

This application claims priority to U.S. Provisional Patent Application Ser. No. 62/924,079, filed Oct. 21, 2019, the entire contents of this application is herein incorporated by reference.

TECHNICAL FIELD

This disclosure relates to systems and methods for predicting biological responses.

BACKGROUND

The mammalian immune system uses two general mechanisms to protect the body against environmental pathogens. When a pathogen-derived molecule is encountered, the immune response becomes activated to ensure protection against that pathogenic organism.

The first immune system mechanism is the non-specific (or innate) inflammatory response. The innate immune system appears to recognize specific molecules that are present on pathogens but not on the body itself.

The second immune system mechanism is the specific or acquired (or adaptive) immune response. Innate responses are fundamentally the same for each injury or infection. In contrast, acquired responses arise specifically in response to molecules in the pathogen, or pathogen-derived molecules. The immune system recognizes and responds to structural differences between self and non-self (e.g. pathogen or pathogen-derived) proteins. Proteins that the immune system recognizes as non-self are referred to as antigens. Pathogens typically express large numbers of highly complex antigens. The acquired immune system leverages two facilities; first, the generation of immunoglobulins (antibodies) in response to many different molecules present in the pathogen, called antigens. The second recruits receptors to bind processed forms of the antigens that are presented on the surface of cells for identification as infected cells by others cells.

Taken together, acquired immunity is mediated by specialized immune cells called B and T lymphocytes (or simply B and T cells). Acquired immunity has specific memory for antigenic structures. Repeated exposure to the same antigen increases the response, which may increase the level of induced protection against that particular pathogen. B cells produce and mediate their functions through the actions of antibodies. B cell-dependent immune responses are referred to as "humoral immunity," because antibodies are found in body fluids. T cell-dependent immune responses are referred to as "cell mediated immunity," because effector activities are mediated directly by the local actions of effector T cells. The local actions of effector T cells are amplified through synergistic interactions between T cells and secondary effector cells, such as activated macrophages. The result is that the pathogen is killed and prevented from causing diseases.

Similar to pathogens, vaccines function by initiating an innate immune response at the vaccination site and activating antigen-specific T and B cells that can give rise to long term memory cells in secondary lymphoid tissues. The precise interactions of the vaccine with cells at the vaccination site and with T and B cells are important to the ultimate success of the vaccine.

In determining if a candidate antigen can be a functional and effective vaccine, the candidate antigen is typically required to undergo rigorous testing and evaluation protocols. Traditionally, a candidate antigen is tested pre-clinically by a process in which the candidate antigen is assessed by in vitro assays, ex vivo assays, and using various animal models (e.g., mouse models, ferret models, etc.).

An example type of assay that can be used to measure a biological response is a hemagglutination inhibition assay (HAI). An HAI applies the process of hemagglutination, in which sialic acid receptors on the surface of red blood cells (RBCs) bind to a hemagglutinin glycoprotein found on the surface of an influenza virus (and several other viruses) and create a network, or lattice structure, of interconnected RBC's and virus particles, referred to as hemagglutination, which occurs in a concentration dependent manner on the virus particles. This is a physical measurement taken as a proxy as to the facility of a virus to bind to similar sialic acid receptors on pathogen-targeted cells in the body. The introduction of anti-viral antibodies raised in a human or animal immune response to another virus (which may be genetically similar or different as the virus used to bind to the RBCs in the assay). These antibodies interfere with the virus-RBC interaction and change the concentration of virus sufficient to alter the concentration at which hemagglutination is observed in the assay. One goal of an HAI can be to characterize the concentration of antibodies in the antiserum or other samples containing antibodies relative to their ability to elicit hemagglutination in the assay. The highest dilution of antibody that prevents hemagglutination is called the HAI titer (i.e., the measured response).

Another example approach to measuring biological responses is to measure a potentially larger set of antibodies elicited by a human or animal immune response, which are not necessarily capable of affecting hemagglutination in the HAI assay. A common approach for this leverages enzyme-linked immunosorbent assay (ELISA) techniques, in which a viral antigen (e.g. hemagglutinin) is immobilized to a solid surface, and then antibodies from the antisera are allowed to bind to the antigen. The readout measures the catalysis of a substrate of an exogenous enzyme complexed to either the antibodies from the antisera, or to other antibodies which themselves bind to the antibodies of the antisera. Catalysis of the substrate gives rise to easily detectable products. There are many variations of this sort of in vitro assay. One such variation is called antibody forensics (AF); which is a multiplexed bead array technique that allows a single sample of serum to be measured against many antigens simultaneously. These measurements characterize the concentration and total antibody recognition, as compared to HAI titers, which are taken to be more specifically related to interference with sialic acid binding by hemagglutinin molecules. Therefore, an antisera's antibodies may in some cases have proportionally higher or lower measurements than the corresponding HAI titer for one virus's hemagglutinin molecules relative to another virus's hemagglutinin molecules; in other words, these two measurements, AF and HAI, are not generally linearly related.

A further example approach to measuring biological responses is to measure the susceptibility of viruses to neuraminidase (NA) inhibitors (NAI Assay). For example, a fluorescence-based assay to assess influenza virus susceptibility to NA inhibitors can be used that is based on the NA enzyme cleaving the 2'-(4-Methylumbelliferyl)-$\alpha$-D-N-acetylneuraminic acid (MUNANA) substrate to release the fluorescent product 4-methylumbelliferone (4-MU). The amount of fluorescence therefore directly relates to the amount of NA enzyme activity. Therefore, the inhibitory effect of an NA inhibitor on the influenza virus NA is determined based on the concentration of the NA inhibitor that is required to reduce 50% of the NA enzyme activity, given as an value commonly referred to as IC(50). The concentration and quality of antibodies in antisera directed against the enzymatic site of NA may thereby be measured as a reduction of NA enzymatic activity in the presence of these antibodies.

Currently, conventional candidate antigen testing may only be performed conditionally given the elicitation of preconceived "protective" immune responses. That is, if one animal or assay fails to demonstrate an appropriate response to the candidate antigen, the candidate antigen is usually "down-selected" (i.e., abandoned as a productive candidate). For example, an influenza antigen is often tested using a sequential selection protocol, where the antigen is first assessed by in vitro assays to ensure that the antigen is facile for large-scale production. Conditional on the antigen passing those requirements, the antigen is then assessed by immunization of, for example, mice to measure its ability to elicit a protective immune response from the mice. This response is usually expected to be protective to the antigen itself and to various other viral strains and/or viral strain components against which protection is desired. Ferrets may thereafter assessed in like manner, conditional on mice or other previous measurements having previously demonstrated what may be taken as suggestive of protective responses. Penultimate to assessment in humans, ex vivo platforms such as human immune system replicas or non-human primates may be assessed; again, conditionally on success in prior steps.

SUMMARY

In an aspect, a data processing system for predicting biological responses is provided. The system includes a computer-readable memory comprising computer-executable instructions. The system includes at least one processor configured to execute executable logic including at least one machine learning model trained to predict biological responses, wherein when the at least one processor is executing the computer-executable instructions, the at least one processor carries out one or more operations. The one or more operations include receiving first sequence data of a first molecular sequence. The one or more operations include receiving second sequence data of a second molecular sequence. The one or more operations include predicting a biological response for the second molecular sequence based at least partly on the received first and second sequence data.

The one or more operations can include receiving non-human biological response data corresponding with the first molecular sequence and the second molecular sequence. The one or more operations can include predicting the biological response is further based at least partly on the non-human biological response data. The one or more operations can include encoding the first sequence data and the second sequence data as amino acid mismatches.

The first molecular sequence can include a candidate antigen. The second molecular sequence can include a known viral strain.

Predicting the biological response can include predicting a human biological response. Predicting the biological response can include predicting at least one human biological response and at least one non-human biological response. The biological response can include an antibody titer. The machine learning model can include a deep neural network.

These and other aspects, features, and implementations can be expressed as methods, apparatus, systems, components, program products, methods of doing business, means or steps for performing a function, and in other ways, and will become apparent from the following descriptions, including the claims.

Implementations of the present disclosure can provide the following advantages. Machine learning techniques can be used to train a machine learning model to predict biological responses, such that incidences of false positives and false negatives are reduced. At least some of the systems and methods described can be used to, when compared with conventional techniques, efficiently process inherently sparse data, for example, by reducing the dimensionality of the data. At least some of the described systems and methods can leverage non-linear relationships in received data to increase prediction accuracy relative to traditional techniques. At least some of the described systems and methods described can be used to simultaneously predict human biological responses and non-human biological responses. At least some of the described systems and methods can be used to predict experimentally unobserved outcomes.

These and other aspects, features, implementations, and advantages can be expressed as methods, apparatus, systems, components, program products, means or steps for performing a function, and in other ways.

These and other aspects, features, and implementations will become apparent from the following descriptions, including the claims.

BRIEF DESCRIPTION OF THE DRAWINGS

FIG. 3 shows an example of data used to train a machine learning model for predicting biological responses, in accordance with one or more embodiments of the present disclosure.

DETAILED DESCRIPTION

Figure 1:
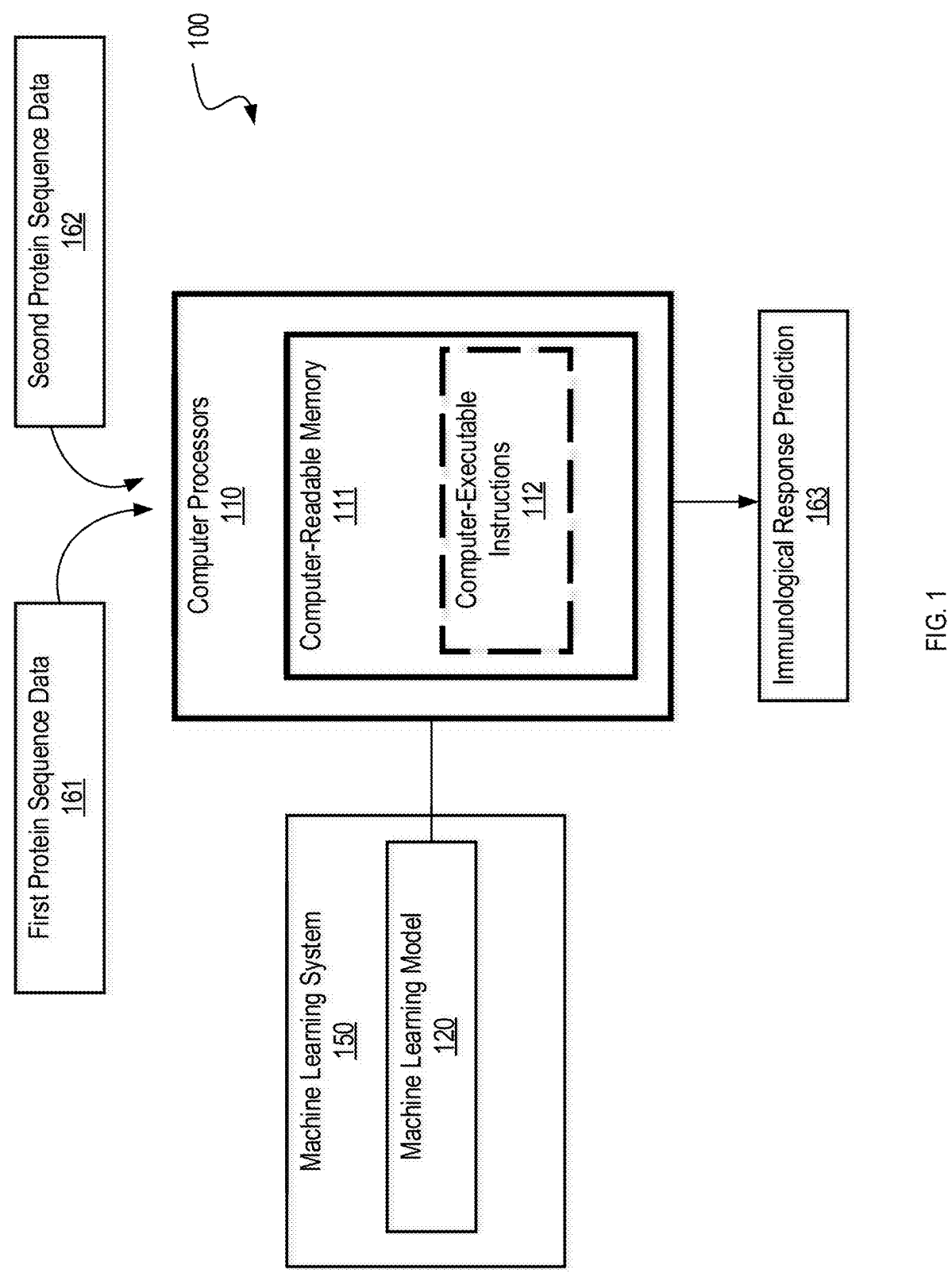
FIG. 1 shows an example of a system for predicting biological responses using machine learning techniques, in accordance with one or more embodiments of the present disclosure.

There can be several critical assumptions in the design of the sequential selection protocols for analyzing candidate vaccinations. One assumption may be that assays are increasingly "translational," by which a qualitative measure of similarity to human responses is assumed. For example, mice are physiologically distant from humans in a variety of aspects (e.g., lifetime, size, organ size, immune system design, etc.). For the case of influenza, ferrets are typically established as a benchmark standard for many aspects of recapitulation of physiological responses to influenza infection (e.g., sneezing, transmission, and so forth). Another assumption may be that poor responses in distant-from-human assessments are necessarily indicative of poor responses in humans. It also may be assumed that good responses in distant-from-human assessments are likely indicative of good responses in more-similar-to-human settings.

Unfortunately, traditional sequential selection protocols may likely lead to the discarding of many antigens that can be effective in humans but fail to elicit the required response in ferret or mouse models (false negatives). Conversely, traditional sequential selection protocols may lead to the selections of antigens that perform well in animals, but will ultimately generate poor responses in humans (false positives).

The systems and methods described in the present disclosure can be used to overcome at least some of the aforementioned disadvantages of traditional sequential selection protocols. For example, the systems and methods described in the present disclosure can use machine learning techniques to train a machine learning model to predict biological responses, such as animal and human responses to toxins or other foreign substances (e.g., influenza antigens). Viral sequence data and biological response readouts from at least one of animal experiments or in vitro experiments can be used to train the machine learning model to make such predictions. Accordingly, the output of the machine learning model can provide insight as to whether a first molecular sequence (e.g., candidate antigen/inoculation strain) can be used to generate a biological response in a human or non-human species that will sufficiently protect the species against other molecular sequences (e.g., known viral strains).

In the drawings, specific arrangements or orderings of schematic elements, such as those representing devices, modules, instruction blocks and data elements, are shown for ease of description. However, it should be understood by those skilled in the art that the specific ordering or arrangement of the schematic elements in the drawings is not meant to imply that a particular order or sequence of processing, or separation of processes, is required. Further, the inclusion of a schematic element in a drawing is not meant to imply that such element is required in all embodiments or that the features represented by such element may not be included in or combined with other elements in some embodiments.

Further, in the drawings, where connecting elements, such as solid or dashed lines or arrows, are used to illustrate a connection, relationship, or association between or among two or more other schematic elements, the absence of any such connecting elements is not meant to imply that no connection, relationship, or association can exist. In other words, some connections, relationships, or associations between elements are not shown in the drawings so as not to obscure the disclosure. In addition, for ease of illustration, a single connecting element is used to represent multiple connections, relationships or associations between elements. For example, where a connecting element represents a communication of signals, data, or instructions, it should be understood by those skilled in the art that such element represents one or multiple signal paths (e.g., a bus), as may be needed, to affect the communication.

Reference will now be made in detail to embodiments, examples of which are illustrated in the accompanying drawings. In the following detailed description, numerous specific details are set forth in order to provide a thorough understanding of the various described embodiments. However, it will be apparent to one of ordinary skill in the art that the various described embodiments may be practiced without these specific details. In other instances, well-known methods, procedures, components, circuits, and networks have not been described in detail so as not to unnecessarily obscure aspects of the embodiments.

Several features are described hereafter that can each be used independently of one another or with any combination of other features. However, any individual feature may not address any of the problems discussed above or might only address one of the problems discussed above. Some of the problems discussed above might not be fully addressed by any of the features described herein. Although headings may be provided, data related to a particular heading, but not found in the section having that heading, may also be found elsewhere in this description.

Systems and Methods for Predicting Biological Responses

FIG. 1 shows an example of a system 100 for predicting biological responses using machine learning techniques, in accordance with one or more embodiments of the present disclosure. The system 100 includes computer processors 110. The computer processors 110 include computer-readable memory 111 and computer readable instructions 112. The system 100 also includes a machine learning system 150. The machine learning system 150 includes a machine learning model 120. The machine learning system 150 may be separate from or integrated with the computer processors 110.

The computer-readable memory 111 (or computer-readable medium) can include any data storage technology type which is suitable to the local technical environment, including, but not limited to, semiconductor based memory devices, magnetic memory devices and systems, optical memory devices and systems, fixed memory, removable memory, disc memory, flash memory, dynamic random-access memory (DRAM), static random-access memory (SRAM), electronically erasable programmable read-only memory (EEPROM) and the like. In some implementations, the computer-readable memory 111 includes code-segment having executable instructions.

In some implementations, the computer processors 110 include a general purpose processor. In some implementations, the computer processors 110 include a central processing unit (CPU). In some implementations, the computer processors 110 include at least one application specific integrated circuit (ASIC). The computer processors 110 can also include general purpose programmable microprocessors, special-purpose programmable microprocessors, digital signal processors (DSPs), programmable logic arrays (PLAs), field programmable gate arrays (FPGA), special purpose electronic circuits, etc., or a combination thereof. The computer processors 110 are configured to execute program code means such as the computer-executable instructions 112. In some implementations, the computer processors 110 are configured to execute the machine learning model 120.

The computer processors 110 are configured to obtain first molecular sequence data 161 of a first molecular sequence and second molecular sequence data 162 of a second molecular sequence. The first molecular sequence data 161 can include amino acid sequence data of a candidate antigen (e.g., inoculation strain). The candidate antigen can correspond, for instance, to the H3N1 virus. The second molecular sequence data 162 can include amino acid sequence data of a known viral strain against which protection is sought. For instance, the second molecular sequence can be a known viral strain that occurred in the year 2001. In some implementations, as will be explained in further detail later with reference to FIG. 4, the computer processors 110 are also configured to receive non-human biological response data associated with the first and second molecular sequences. The non-human biological response data can include, for example, biological response readouts (e.g., antibody titers) that measure the biological response of a non-human model (e.g., mouse, ferret, human immune system replica, etc.) to the second molecular sequence after being inoculated with the first molecular sequence. As discussed later in further detail with reference to FIG. 4, in some implementations, the computer processors 110 are capable of encoding the first molecular sequence data 161 and the second molecular sequence data 162 as amino acid mismatches. The afore-mentioned data can be obtained through one or more means, such as wired or wireless communications with databases (including cloud-based environments), optical fiber commu-nications, Universal Serial Bus (USB), compact disc read-only memory (CD-ROM), and so forth.

The machine learning system 150 applies machine learn-ing techniques to train the machine learning model 120 that, when applied to the input data, generates indications of whether the input data items have the associated property or properties, such as probabilities that the input data items have a particular Boolean property, or an estimated value of a scalar property.

As part of the training of the machine learning model 120 the machine learning system 150 can form a training set of input data by identifying a positive training set of input data items that have been determined to have the property in question, and, in some implementations, forms a negative training set of input data items that lack the property in question.

The machine learning system 150 extracts feature values from the input data of the training set, the features being variables deemed potentially relevant to whether or not the input data items have the associated property or properties. An ordered list of the features for the input data is herein referred to as the feature vector for the input data. In some implementations, the machine learning system 150 applies dimensionality reduction (e.g., via linear discriminant analy-sis (LDA), principle component analysis (PCA), learned deep features from a neural network, or the like) to reduce the amount of data in the feature vectors for the input data to a smaller, more representative set of data.

In some implementations, the machine learning system 150 uses supervised machine learning to train the machine learning model 120 with the feature vectors of the positive training set and the negative training set serving as the inputs. Different machine learning techniques—such as lin-ear support vector machine (linear SVM), boosting for other algorithms (e.g., AdaBoost), neural networks, logistic regression, naïve Bayes, memory-based learning, random forests, bagged trees, decision trees, boosted trees, or boosted stumps—are used in some implementations. The machine learning model 120, when applied to the feature vector extracted from the input data item, outputs an indi-cation of whether the input data item has the property in question, such as a Boolean yes/no estimate, a scalar value representing a probability, a vector of scalar values repre-senting multiple properties, or a nonparametric distribution of scalar values representing different and not a priori fixed numbers of multiple properties, which may be represented either explicitly or implicitly in a Hilbert or similar infinite dimensional space.

In some implementations, a validation set is formed of additional input data, other than those in the training sets, which have already been determined to have or to lack the property in question. The machine learning system 150 applies the trained machine learning model 120 to the data of the validation set to quantify the accuracy of the machine learning model 120. Common metrics applied in accuracy measurement include: Precision=TP/(TP+FP) and Recall=TP/(TP+FN), where precision is how many the machine learning model 120 correctly predicted (TP or true positives) out of the total it predicted (TP+FP or false positives), and recall is how many the machine learning model 120 correctly predicted (TP) out of the total number of input data items that did have the property in question (TP+FN or false negatives). The F score (F-score=2*PR/(P+R)) unifies precision and recall into a single measure. In some implementations, the machine learning system 150 iteratively re-trains the machine learning model 120 until the occurrence of a stopping condition, such as the accuracy measurement indication that the model 120 is sufficiently accurate, or a number of training rounds having taken place.

In some implementations, the machine learning model 120 includes a neural network. In some implementations, the neural network includes a convolutional neural network. The machine learning model 120 can include other types of neural networks, such as recurrent neural networks, radial basis function neural networks, physical neural networks (e.g., optical neural network), and so forth. Particular meth-ods of training the machine learning model according to one or more implementations of the present disclosure are dis-cussed later in more detail with reference to FIGS. 3-4.

The machine learning model 120 is configured to predict, based on the received data, a biological response 163 for the second molecular sequence. For example, assume that the first molecular sequence data 161 represents an amino acid sequence of a candidate antigen that is to be used as a vaccination and the second molecular sequence data 162 represents an amino acid sequence of a viral strain known to have been in circulation in the year 2012. The machine learning model 120 can predict a biological response (e.g., an antibody titer) that a human immune system will generate after encountering the second molecular sequence (e.g., known viral strain) if the human immune system was inoculated with the first molecular sequence (i.e., candidate antigen).

Figure 2:
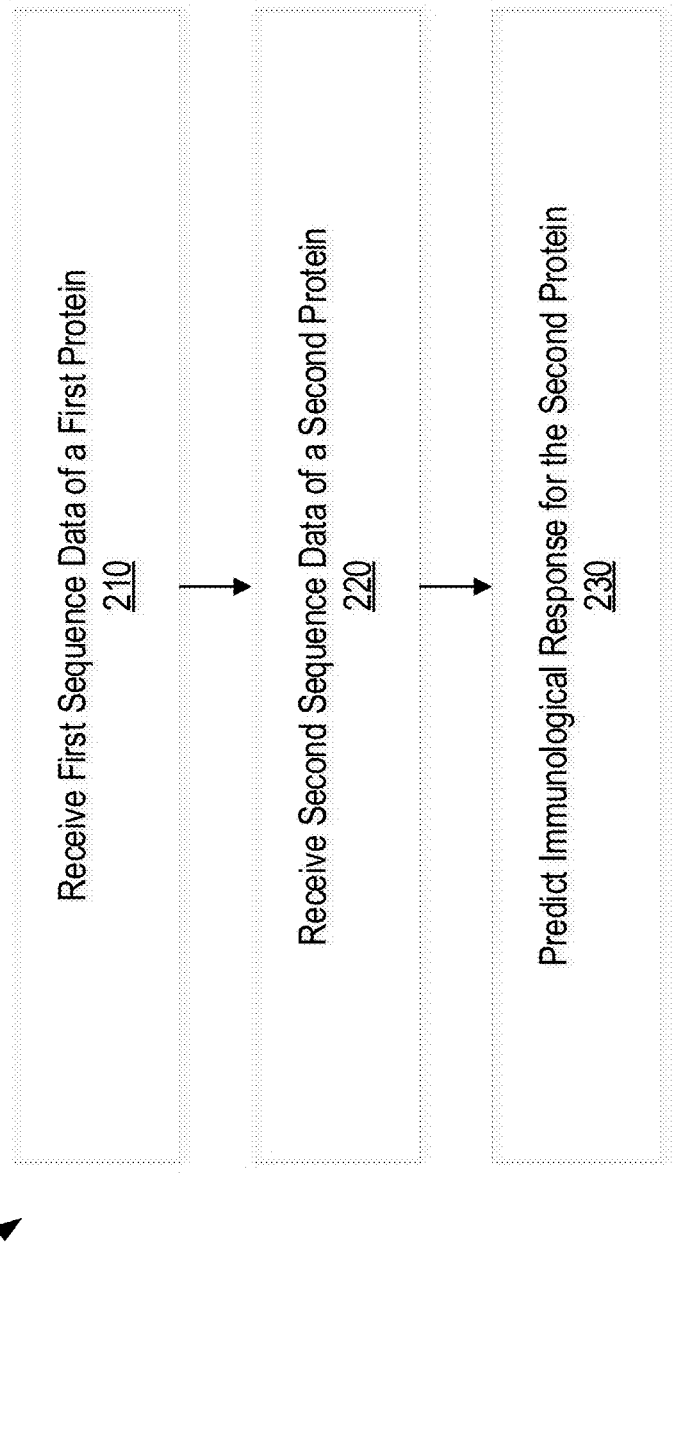
FIG. 2 shows a flowchart depicting an example of a method for predicting biological responses, in accordance with one or more embodiments of the present disclosure.

FIG. 2 shows a flowchart depicting an example of a method 200 for predicting biological responses using machine learning techniques, in accordance with one or more implementations of the present disclosure. For illus-trative purposes, the method 200 is described as being performed by the system 100 for predicting biological responses using machine learning techniques discussed ear-lier with reference to FIG. 1. The method 200 includes receiving first sequence data of a first molecular sequence (block 210), receiving second sequence data of a second molecular sequence (block 220), and predicting a biological response for the second molecular sequence (block 230).

At block 210, the computer processors 110 receive the first molecular sequence data 161 of the first molecular sequence. As previously indicated, the first molecular sequence data 161 can include amino acid sequence data of a candidate antigen (e.g., inoculation strain). For instance, the candidate antigen can correspond to the H3N1 virus.

At block 220, the computer processors 220 receive the second molecular sequence data 162 of the second molecu-lar sequence. The second molecular sequence data 162 can include amino acid sequence data of a known viral strain against which protection is sought. For instance, the second molecular sequence can be a known viral strain that occurred in the year 2001.

In some implementations, the method 200 further includes encoding the first molecular sequence data 161 and the second molecular sequence data 162 as amino acid mismatches. For example, similar regions of the first molecular sequence and the second molecular sequence can be compared, and a value of "1" can be encoded for each non-matching amino acid pairing in the regions, while a value of "0" can be encoded for each matching amino acid pairing in the region. Thus, the dissimilarity between the first molecular sequence and the second molecular sequence, as defined by non-matching amino acids at locations within a similar region between the molecular sequences, can be provided to the machine learning model 120.

In some implementations, the method 200 further includes receiving non-human biological response data associated with the first and second molecular sequences. The non-human biological response data can include, for example, biological response readouts (e.g., antibody titers) that measure the biological response of a non-human model (e.g., mouse, ferret, replica human immune systems, etc.) to the second molecular sequence after being inoculated with the first molecular sequence.

At block 230, the machine learning model 120 predicts a biological response for the second molecular sequence based on the received data. For example, the machine learning model 120 can predict a biological response (e.g., an antibody titer) that a human immune system will generate after encountering the second molecular sequence (i.e., known viral strain) if the human immune system was inoculated with the first molecular sequence (i.e., candidate antigen). In some implementations, the machine learning model 120 is configured to predict a non-human biological response for the second molecular sequence. For instance, the machine learning model can predict an antibody titer that an animal's immune system (e.g., mouse, ferret, etc.) will generate after encountering the second molecular sequence if the animal's immune system was inoculated with the first molecular sequence.

Methods of Training Machine Learning Models for Predicting Biological Responses

Methods for training the machine learning model 120 to predict biological responses will now be described. FIG. 3 shows an example of data used to train a machine learning model for predicting biological responses, in accordance with one or more implementations of the present disclosure. As shown, data from thousands (or millions, billions, etc.) of experiments can be used to build a comprehensive repository of biological response readouts and viral sequence data from, for example, ferret, mouse, and in vitro human immune system replica (e.g., MIMIC®) models. In the shown embodiment, the data includes antigen sequence data, viral sequence data, and biological response readouts as measured by hemagglutination inhibition assay (HAI) and antibody forensics (AF). The viral sequence data includes a panel of known viral strains (referred to as a "read-out" panel). The experiments can be separated into batches referred to as "cycles" (e.g., cycle 1 and cycle 2). In each cycle, the model systems are challenged with selected molecular sequences (e.g., H3 proteins, vaccine preparations, etc.) and measured for their ability to generate an immune response against a panel of "read-out" viral strains (referred to as a "read-out panel"). The viral read-out panels can be selected to represent a broad sampling of influenza strains that were in circulation during a defined period of years (e.g., 1950 to 2016).

To associate the model experiments with human results, human sera can be measured against the "read-out" panel. In the shown example, for every pair of antigen-strain/readout-strain tested in the model systems, there is not always a corresponding pair in the human serum measurements. This is because human samples may be collected from people vaccinated during periods that don't cover the full period of years used for each of the cycles. Accordingly, the machine learning model can be restricted to only the antigens and readouts tested in human sera, and a vector of human readout titers can be selected as the target vector for the machine learning model. The human AF readouts can be from human sera collected at Day 21 post-vaccination, which is usually sufficient time for a subject to seroconvert after inoculation.

Using the resulting data from the aforementioned experiments, a model can be trained to predict biological responses. In some implementations, a linear model can be used.

Figure 4:
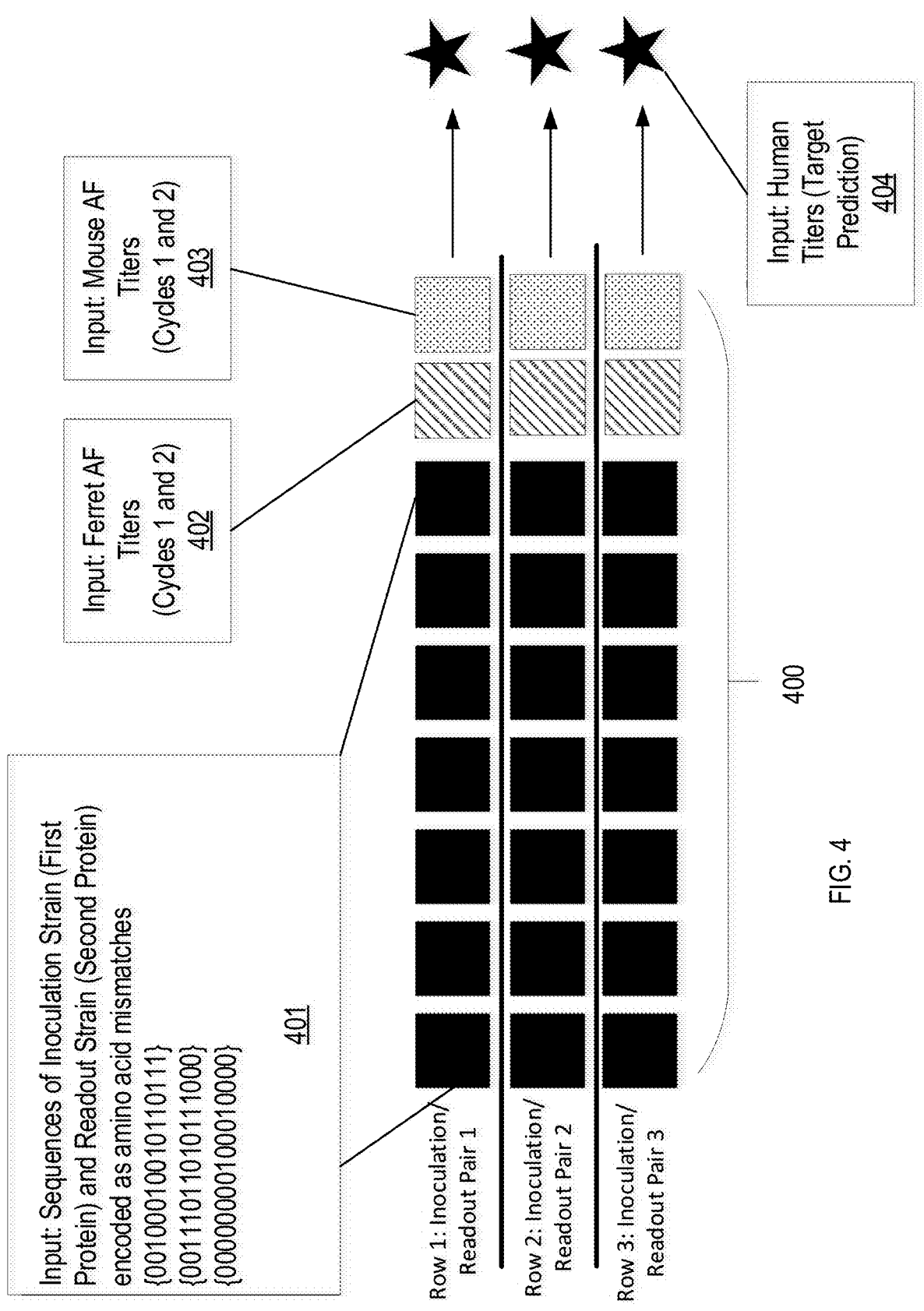
FIG. 4 shows a flow diagram of an example for training a machine learning model for predicting biological responses, in accordance with one or more embodiments of the present disclosure.

FIG. 4 shows a flow diagram of an example for training a machine learning model for predicting biological responses, in accordance with one or more implementations of the present disclosure. As shown, a data matrix 400 is first prepared where each row corresponds to a pair of virus antigens, such as the H3 regions of the antigen strain and the "read-out" strain. The columns (or features) of the matrix include specific columns for the ferret model AF readout titers 402 and the mouse model AF readout titers 403. In some implementations, missing titer data is imputed with the mean value of the column. However, any number of standard methods may be used to impute missing titer data. The sequence columns 401 represent an amino acid sequence difference (SeqDiff) representation between the antigen strain and "read-out" strain in a selected region, which in the shown example includes the H3 regions of the antigen and "read-out" strain. A SeqDiff is prepared by checking, at each position of an H3 amino acid sequence alignment, whether the amino acid is the same or different between the antigen and "read-out" strain. If the amino acids between the two strains are not the same, a "1" can be encoded. If the amino acids between the two strains are the same, a "0" can be encoded. Encoding the two sequences as amino acid mismatches can essentially create a protein hamming distance measure, which generally reflects the number of positions at which the corresponding amino acids are different. In some implementations, columns that are consistently "0" across the entire training set are discarded. The columns 401, 402, 403 of each row are associated with a corresponding human titer 404 using linear regression.

Columns 402, 403 including readout titers can be, for example, z-score transformed before fitting a linear regression model. Z-scores can refer to linearly transformed data values having a mean of zero and a standard deviation of one, and can indicate how many standard deviations an observation is above or below the mean. Because the encoding of the SeqDiff representation can be sparse, in some instances, Principle Component Analysis (PCA) can be used to reduce the dimensionality of the SeqDiff vectors to five components. PCA refers to a statistical procedure that uses an orthogonal transformation to convert a set of observations of possibly correlated variables into a set of values of linearly uncorrelated variables called principal components. PCA can be used to emphasize variation, highlight strong patterns in datasets, and reduce a large set of variables to a smaller set without losing a significant amount of information in the larger set. The linear model can be trained on various combinations of the data to better understand the relative abilities of mouse titers, ferret titers, and sequence data to predict human responses.

While, as previously described, the machine learning model can be built as a linear model to predict the biological responses, it is possible that non-linear relationships exist between the data features and the human biological responses. Accordingly, using the data from the aforementioned experiments, a model using a deep neural network, or other nonlinear models, can be built that is capable of 1) leveraging non-linear relationships in the data to make relatively accurate predictions when compared to the aforementioned linear model and 2) making predictions for both animal and human titers simultaneously. Predicting all titers together can exploit the realization that a strong signal for immune response may be encoded directly in the protein sequences of the antigen & "read-out" strains. By training the model to predict both human and animal titers from sequence alone, the machine learning model can be forced to search for sequence-function relationships that drive immunogenicity across species. In statistical terms, this may be referred to as "borrowing strength," and can allow the model to better leverage large amounts of available data for one type of model (e.g., ferret model) to generate more robust predictions for human responses. This strategy can accommodate more viral antigens and the building of a data matrix with over 13000 example rows. As with the linear models, the SeqDiff representation of the H3 regions for each viral and readout strain pair can be used as input data.

While, in some implementations, the target vector is human titers for the linear model, the non-linear neural network model can represent a multi-target regression problem with, for example, seven output columns (Ferret HAI & AF titers, Mouse HAI and AF titers, MIMIC AF, Human HAI, Human AF). Because the limit of detection for HAI experiments may typically be 40 (or, when expressed as a dilution, 1:40), any measurements falling below this value can be set to 40. Similarly, AF measurements can be set to 10000 if they fall below that value. HAI can be expressed as log 2(titer/10), while AF can be expressed as log 2(titer). Human and human replica data may have an extra level of complexity if measurements are made at the time of inoculation (Day 0) and post-seroconversion (Day 21). Accordingly, human and human replica titers can be expressed as a log 2 fold-change of Day 21/Day 0. In cases where titer values are missing in the target vectors, those values can be set to zero and the loss function in the neural network can be masked for those positions. This can ensure that predictions for missing values do not contribute to the fitness of the model during training.

In some implementations, a neural network having two 128-node dense layers with relu activation, and a 7-node dense output layer can be used. Portions of the data (for example, fifteen percent of the data) can be randomly excluded as a test set and the neural network network can be trained for a number of epochs (for example 400, 500, 1000, etc.). In some implementations, the following parameters are used: learning rate=0.001; weight-decay=0.0001; batch size=128.

In some implementations, an L2 loss function is used for human replica, human AF, and human HAI target vectors. Generally, an L2 loss function minimizes the squared differences between the estimate target values and the existing target values. In some implementations, a Huber loss function can be used for ferret and mouse data. Generally, a Huber loss function is used in robust regression, and, in at least some instances, can be less sensitive to outliers in data than the L2 loss function. To further bias the model, an explicit weighting scheme can be used to apply an additional penalty to misclassified human samples. For example, the following weights can be multiplied by each target loss at each epoch of training: Ferret HAI=0.8; Ferret AF=1; Mouse HAI=1; Mouse AF=1; Human HAI=2; Human AF=2; MIMIC=1.5.

Figure 5:
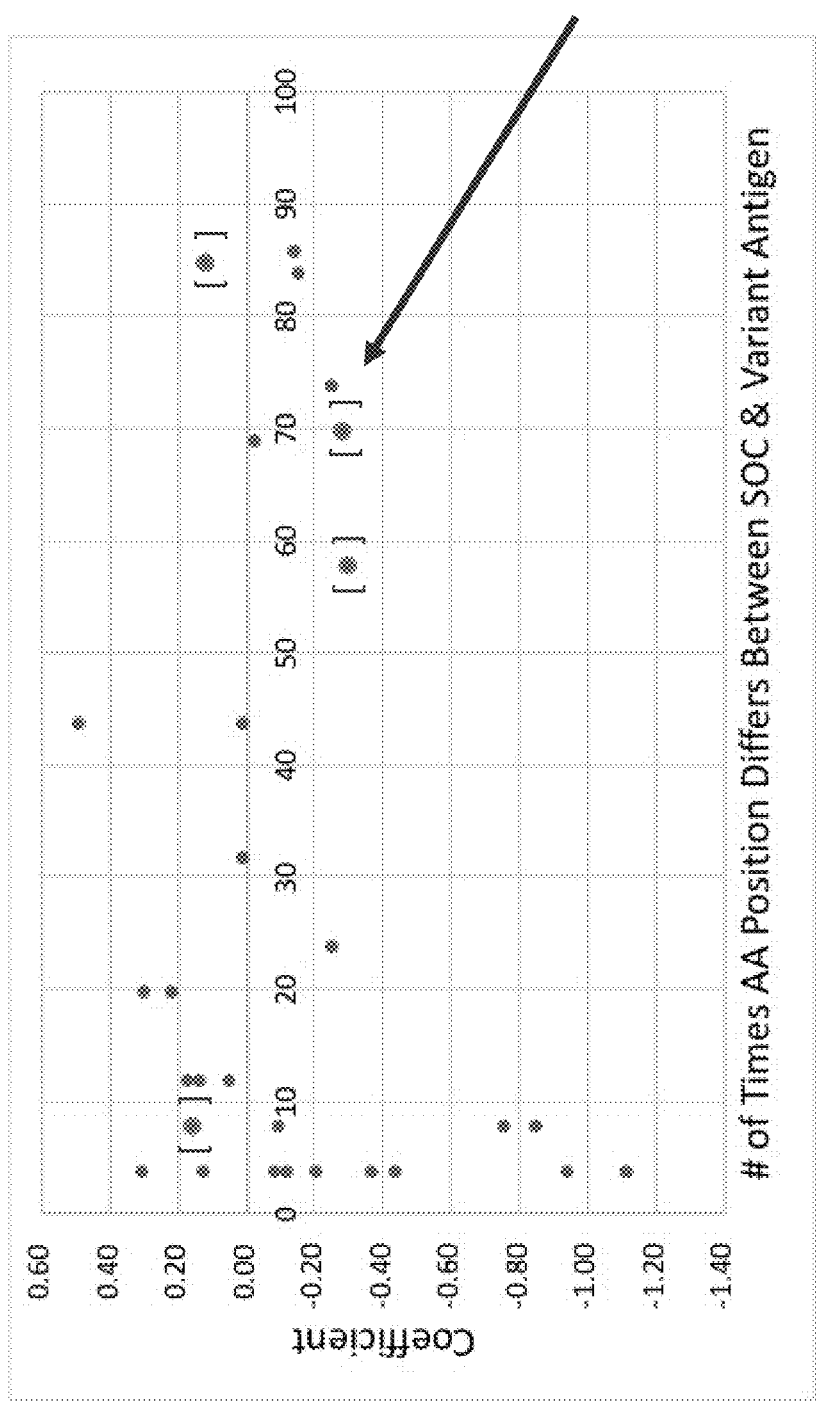
FIG. 5 depicts experimental results of a translational model developed to predict biological responses.

Experimental Results:

FIG. 5 depicts experimental results of a translational model developed to predict biological responses. A sequence delta model was developed that uses a per-sequence-position mismatch (I/O) of an antigen sequence and an antibody-inducing antigen sequence to predict, by regression, whether said antibody inhibits the antigen neuraminidase enzyme. Measurements of NAI of mouse sera antibodies induced by four standard-of-care (SOC) neuraminidase antigens against 42 NA variants, and the resulting normalized IC50 calculation for each sera-NA variant part, were used to train the model. As indicated previously, the model includes features such as sequence mismatches between sera SOC-variant antigen pairs encoded by 1 or 0. Linear regression was applied to the sequence features to predict an antibody-antigen NAI as normalized IC50s. As shown in FIG. 5, most NA sequence variations reduced SOC antibody NAI (relative to SOC NA), as evident by the negative coefficients, and were approximately twice as likely to border active sites, suggest the model was capturing accurate biological functions.

While the foregoing description describes certain candidate antigens, and their associated biological responses, in the context of influenza, the term antigen is understood to be construed broadly to encompass any toxin or foreign substance which induces an immune response in the body (e.g., the production of antibodies). For example, an antigen can correspond to a viral strain, a bacterial strain, a protozoan strain, a prion strain, a viroid strain, or a fungal strain, among others. For example, a candidate antigen can correspond to the respiratory syncytial virus, and other paramyxoviruses. A candidate antigen can include a Pertussis antigen, a Diphtheria antigen, and a Tetanus antigen, among others.

While the foregoing description describes certain biological responses, such as HAI titers and AF titers, other biological responses can be used. For example, a biological response can correspond to antibody characterizations, such as affinity and/or avidity against specific antigens and/or panels of antigen fragments (e.g. protein arrays, phage display libraries, and the like), functional profiling such as to determine anti-drug-antibodies, immune complement interaction (e.g. phagocytosis, inflammation, membrane attack), antibody-dependent cellular cytotoxicity (ADCC) or similar Fc-mediated effector functions, profiling of immune complexes formed (e.g. receptor-binding profiles), immunoprecipitation assays, NA enzyme inhibition, or combinations of these. A biological response can correspond to competition of an antibody binding to a target by other antibodies, or antisera. A biological response can correspond to antisera characterizations, which can correspond to those of the aforementioned antibody characterizations, and functional assays (such as microneutralization assays, hemagglutination inhibition, and neuraminidase inhibition), binding assays (such as hemagglutination assays), enzymatic reaction assays (such as enzyme-linked lectin assays (ELLA)), ligand binding assays (such as binding of sialic acid derivatives and their mimetics), and fluorescent readout assays (such as 20-(4-methylumbelliferyl)-a-D-N-acetyl-neuraminic acid (MUNANA) cleavage).

A biological response can correspond to in vivo assessments leveraging either monoclonal or polyclonal antibodies through passive transfer and/or exogenous expression or transfer achieved by one or more of the following: transfection or endogenous expression mediated by retroviral infection, or host genome modification such as through CRISPR, fluid transfer between two bodies, or combinations of these. A biological response can correspond to in vivo assessments of immunity raised through immunization to assess antigenicity. A biological response can correspond to characterizations such as binding/affinity measurements of linear peptide antigens on major histocompatibility complex (MHC) class I and class II), and also to assess productive T-cell epitope display for recognition by T-cells. A biological response can correspond to characterizations such as affinity against panels of antigen fragments (e.g. protein arrays, phage display libraries, and the like) to identify epitopes being recognized. A biological response can correspond to functional profiling ex vivo and/or in vitro such as to determine T-cell responses and/or responses mediated. A biological response can correspond to in vivo and/or in situ measurements of proliferation (e.g. abundance in tissue compartments) in response to natural infection and/or challenge and/or immunization of adaptive-response associated T-cells (e.g. $\alpha\beta$ or $\gamma\delta$ T-cells). A biological response can correspond to in vitro and/or ex vivo measurements of specificity in recognition by adaptive-response associated T-cells (e.g. $\alpha\beta$ or $\gamma\delta$ T-cells) in response to natural infection and/or challenge and/or immunization as measured by competition with other epitopes.

A biological response can correspond to in situ, ex vivo and/or in vivo assessments of morphology or physiological changes to tissue formation, tissue repair, or tissue invasion by a pathogen to be protected against or a proxy such as pseudotyped viruses or bacteria. A biological response can correspond to in situ, ex vivo protein, gene expression, and/or non-coding RNA level differences relative to other antigens and/or physiological status as characterized, for example, by biomarkers such as age, gender, frailty, nominal serostatus, race, haplotype, geographic location. A biological response can correspond to in situ assessments of protection, transmission, or other gross physiological responses to infection either naturally occurring or through transmission in humans or model organisms such as, but not restricted to mouse, rat, rabbit, ferret, guinea pig, pig, cow, chicken, sheep, porpoises, bat, dog, cat, zebrafish and other teleosts, and nonhuman primates such as monkeys and great apes.

With respect to response deliberate infection (i.e. challenge) with homotypic and/or heterotypic infectious agents, including in controlled human challenge studies, a biological response can correspond to in situ, ex vivo, and/or in vivo assessments of proteins or metabolites present in blood or tissues, in which the proteins may be cytokines, hormones, or signaling molecules, and in which the metabolites may be vitamins, cofactors, or other metabolic by-products. A biological response can correspond to in situ, ex vivo, and/or in vivo assessments of a microbiome that may be affected by or impact the immune response. A biological response can correspond to functional profiling ex vivo, in vitro phenotypic, and/or functional T-cell response profiling (receptor expression, cytokine production, cytotoxic potential) in response to challenge with antigen alone or antigen in conjunction with innate immune cells (such as natural killer (NK) cells, dendritic cells (DCs), neutrophils, macrophages, monocytes, and so forth). A biological response can correspond to epigenetic analysis performed using samples collected or generated using techniques or methods as previously described.

While the foregoing description describes certain methods and data for training a machine learning model to predict biological responses, other methods and data can be used. For example, the neural network model can include more or fewer layers than the models previously described, where each layer can have more or less nodes.

In the foregoing description, embodiments of the invention have been described with reference to numerous specific details that may vary from implementation to implementation. The description and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction. Any definitions expressly set forth herein for terms contained in such claims shall govern the meaning of such terms as used in the claims. In addition, when we use the term "further comprising," in the foregoing description or following claims, what follows this phrase can be an additional step or entity, or a sub-step/sub-entity of a previously-recited step or entity.

What is claimed is:

1. A data processing system for predicting biological responses, the system comprising:

one or more computers; and one or more computer-readable storage devices communicatively coupled to the one or more computers, wherein the one or more storage devices store computer-executable instructions that, when executed by the one or more computers, cause the one or more computers to perform operations comprising:

receiving first sequence data of a first molecular sequence associated with a candidate antigen;

receiving second sequence data of a second molecular sequence associated with a viral strain; and generating, as a model input to a machine learning model, an input feature vector that combines: (i) the first sequence data of the first molecular sequence associated with the candidate antigen, (ii) the second sequence data of the second molecular sequence associated with the viral strain, and (iii) one or more non-human biological response scores, wherein each non-human biological response score characterizes an experimentally measured response that a non-human immune system generates after encountering the viral strain post-inoculation with the candidate antigen; and processing the input feature vector combining (i) the first sequence data of the first molecular sequence associated with the candidate antigen, (ii) the second sequence data of the second molecular sequence associated with the viral strain, and (iii) the one or more non-human biological response scores, using the machine learning model and in accordance with values of a set of machine learning model parameters, to generate a predicted human biological response score, wherein the predicted human biological response score characterizes a predicted response that a human immune system will generate after encountering the viral strain represented by the model input if the immune system was previously inoculated with the candidate antigen represented by the model input; and wherein the set of machine learning model parameters have been trained by a machine learning training technique on a set of training data comprising a plurality of training antigen-training viral strain pairs, wherein for each pair, the training data includes an experimentally measured biological response score generated by:

(a) inoculating a human subject with the training antigen, (b) exposing the human subject to the training viral strain post-inoculation with the training antigen, and (c) measuring an immune response of the human subject upon exposure to the training viral strain to determine the experimentally measured biological response score reflecting conditioning by prior antigen exposure.

2. The system of claim 1, wherein the operations further comprise encoding the first sequence data and the second sequence data as amino acid mismatches.

3. The system of claim 1, wherein the machine learning model generates at least one human biological response score and at least one non-human biological response score.

4. The system of claim 1, wherein the machine learning model comprises a deep neural network.

5. The system of claim 1, wherein the predicted biological response score defines a predicted antibody titer.

6. The system of claim 1, wherein the viral strain is an influenza viral strain.

7. The system of claim 1, wherein the model input to the machine learning model comprises a non-human biological response score for in a mouse immune system, or a non-human biological response score in a ferret immune system, or both.

8. A method performed by one or more computers, the method comprising:

receiving first sequence data of a first molecular sequence associated with a candidate antigen;

receiving second sequence data of a second molecular sequence associated with a viral strain; and generating, as a model input to a machine learning model, an input feature vector that combines: (i) the first sequence data of the first molecular sequence associated with the candidate antigen, (ii) the second sequence data of the second molecular sequence associated with the viral strain, and (iii) one or more non-human biological response scores, wherein each non-human biological response score characterizes an experimentally measured response that a non-human immune system generates after encountering the viral strain post-inoculation with the candidate antigen; and processing the input feature vector combining (i) the first sequence data of the first molecular sequence associated with the candidate antigen, (ii) the second sequence data of the second molecular sequence associated with the viral strain, and (iii) the one or more non-human biological response scores, using the machine learning model and in accordance with values of a set of machine learning model parameters, to generate a predicted human biological response score, wherein the predicted human biological response score characterizes a predicted response that a human immune system will generate after encountering the viral strain represented by the model input if the immune system was previously inoculated with the candidate antigen represented by the model input; and wherein the set of machine learning model parameters have been trained by a machine learning training technique on a set of training data comprising a plurality of training antigen-training viral strain pairs, wherein for each pair, the training data includes an experimentally measured biological response score generated by:

(a) inoculating a human subject with the training antigen, (b) exposing the human subject to the training viral strain post-inoculation with the training antigen, and (c) measuring an immune response of the human subject upon exposure to the training viral strain to determine the experimentally measured biological response score reflecting conditioning by prior antigen exposure.

9. The method of claim 8, further comprising encoding the first sequence data and the second sequence data as amino acid mismatches.

10. The method of claim 8, wherein the machine learning model generates at least one human biological response score and at least one non-human biological response score.

11. The method of claim 8, wherein the machine learning model comprises a deep neural network.

12. The method of claim 8, wherein the predicted biological response score defines a predicted antibody titer.

13. The method of claim 8, wherein the viral strain is an influenza viral strain.

14. The method of claim 8, wherein the model input to the machine learning model comprises a non-human biological response score for in a mouse immune system, or a non-human biological response score in a ferret immune system, or both.

15. One or more non-transitory computer storage media storing instructions that when executed by one or more computers cause the one or more computers to perform operations comprising:

receiving first sequence data of a first molecular sequence associated with a candidate antigen;

receiving second sequence data of a second molecular sequence associated with a viral strain; and generating, as a model input to a machine learning model, an input feature vector that combines: (i) the first sequence data of the first molecular sequence associated with the candidate antigen, (ii) the second sequence data of the second molecular sequence associated with the viral strain, and (iii) one or more non-human biological response scores, wherein each non-human biological response score characterizes an experimentally measured response that a non-human immune system generates after encountering the viral strain post-inoculation with the candidate antigen; and processing the input feature vector combining (i) the first sequence data of the first molecular sequence associated with the candidate antigen, (ii) the second sequence data of the second molecular sequence associated with the viral strain, and (iii) the one or more non-human biological response scores, using the machine learning model and in accordance with values of a set of machine learning model parameters, to generate a predicted human biological response score, wherein the predicted human biological response score characterizes a predicted response that a human immune system will generate after encountering the viral strain represented by the model input if the immune system was previously inoculated with the candidate antigen represented by the model input; and wherein the set of machine learning model parameters have been trained by a machine learning training technique on a set of training data comprising a plurality of training antigen-training viral strain pairs, wherein for each pair, the training data includes an experimentally measured biological response score generated by:

(a) inoculating a human subject with the training antigen, (b) exposing the human subject to the training viral strain post-inoculation with the training antigen, and (c) measuring an immune response of the human subject upon exposure to the training viral strain to determine the experimentally measured biological response score reflecting conditioning by prior antigen exposure.

16. The non-transitory computer storage media of claim 15, wherein the operations further comprise encoding the first sequence data and the second sequence data as amino acid mismatches.

17. The non-transitory computer storage media of claim 15, wherein the machine learning model generates at least one human biological response score and at least one non-human biological response score.

18. The non-transitory computer storage media of claim 15, wherein the machine learning model comprises a deep neural network.

19. The non-transitory computer storage media of claim 15, wherein the viral strain is an influenza viral strain.

20. The non-transitory computer storage media of claim 15, wherein the model input to the machine learning model comprises a non-human biological response score for in a mouse immune system, or a non-human biological response score in a ferret immune system, or both.

* * * * *